United States Patent [19]
Friedman et al.

[11] Patent Number: 4,743,552
[45] Date of Patent: May 10, 1988

[54] METHOD FOR GROWTH IN TISSUE CULTURE OF NORMAL COLONIC EPITHELIAL CELLS AND METHOD FOR DETERMINATION OF PRENEOPLASTIC COLOR CELLS

[75] Inventors: Eileen A. Friedman; Martin Lipkin, both of New York, N.Y.

[73] Assignee: Sloan-Kettering Institute for Cancer Research, New York, N.Y.

[21] Appl. No.: 655,090

[22] Filed: Sep. 26, 1984

[51] Int. Cl.⁴ ............................ C12N 5/00; C12Q 1/02
[52] U.S. Cl. .................................. 435/240.23; 435/29; 435/30; 435/34; 435/35; 435/244
[58] Field of Search ................... 436/504; 435/29, 30, 435/34, 35, 240, 244, 240.21, 240.23

[56] References Cited

U.S. PATENT DOCUMENTS 4,317,877  3/1982  Balis et al. .............................. 435/7

OTHER PUBLICATIONS

Chemical Abstracts, vol. 95, #216200z, 1981.
Mayer et al., Science vol. 224, No. 4656, pp. 1445–1447, 1984.
Chemical Abstracts, vol. 101, #187419n, 1984.
Methods in Enzymology, Cell Culture Techniques, vol. LVIII ed. by Jakoby & Pastan, pp. 124–137, 1979.
Friedman et al., Cancer Research 44:4078 (1984).
Moyer, M. P. et al., (1983) Proc. of the Soc. for Exp. Bio. and Medicine 174:12–15.
Deschner, E., et al., (1975) Cancer 35:413–418.
Lipkin, M., et al., (1974) Cancer 34:878–888.
Lipkin, M., et al., (1983) Cancer Research, 43:1899–1904.
Friedman, E., (1981) Cancer Research 41:4588–4599.
Friedman, E., et al., (1981) in vitro 17:632–644.
Friedman, et al., (1984) Cancer Res. 44:1568.
Yuspa, et al., (1982) Cancer Res. 42:2344.

*Primary Examiner*—Christine M. Nucker
*Attorney, Agent, or Firm*—John P. White

[57] ABSTRACT

The invention concerns a method for the routine primary culture of human colonic epithelial cells within a monolayer. 12-0-tetradecanoylphorbol-13-acetate (TPA) enhanced DNA synthesis an average of 8 fold when assayed by [³h]dThd labeling indices (L.I.) in colonic epithelial cells from familial polyposis patients and in tubular adenomas. No such stimulation by TPA was seen in cells from high-risk patients without familial polyposis, or in cells from low-risk subjects.

2 Claims, 1 Drawing Sheet

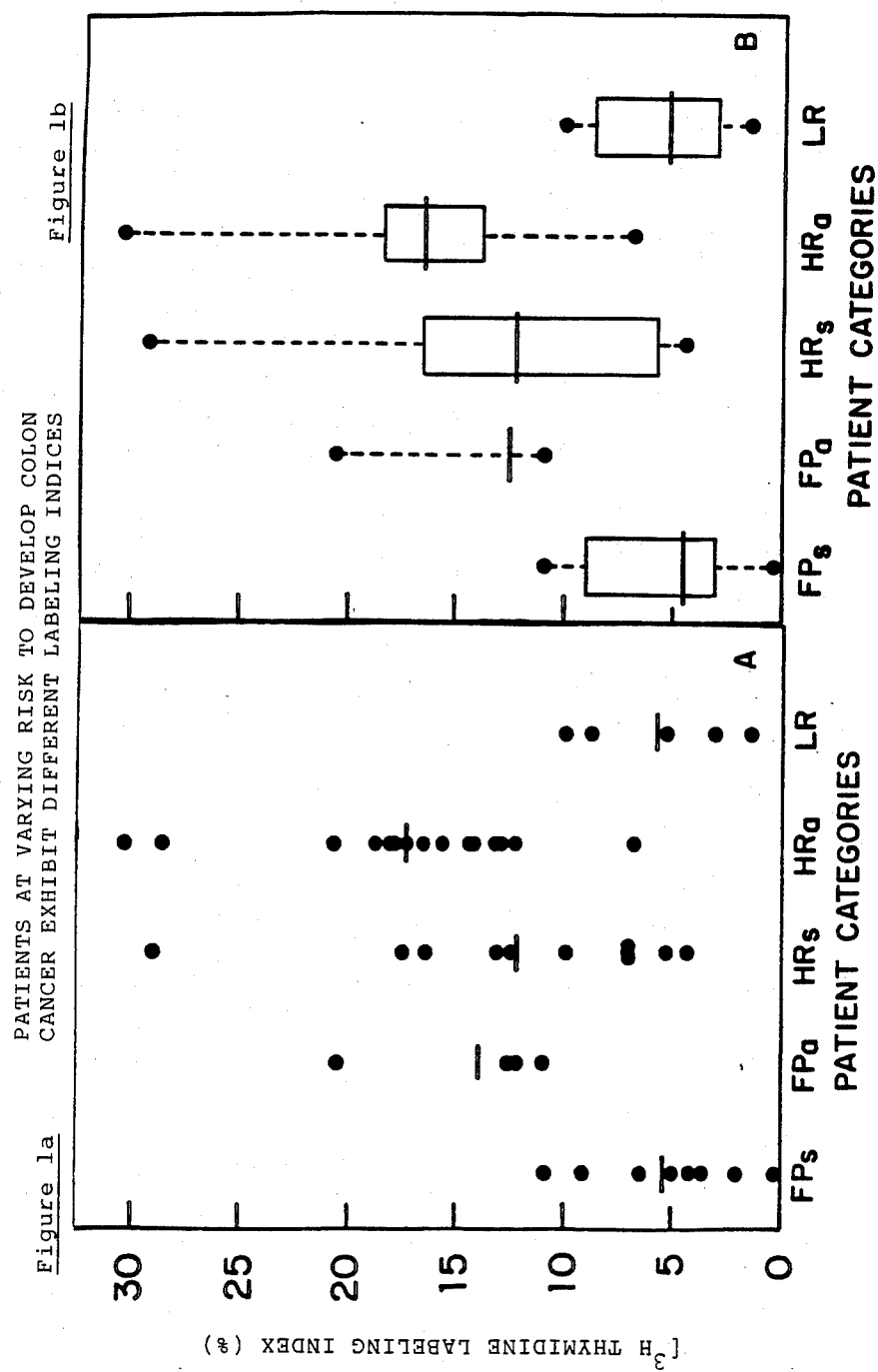

METHOD FOR GROWTH IN TISSUE CULTURE OF NORMAL COLONIC EPITHELIAL CELLS AND METHOD FOR DETERMINATION OF PRENEOPLASTIC COLOR CELLS

This work was funded in part by United States Public Health Service (USPHS) grants 28822 from the National Large Bowel Cancer Project and 08748 from the National Cancer Institute, Department of Health and Human Services. Therefore, the U.S. government has certain rights in this invention.

BACKGROUND

Human colonic epithelial cells have proven rather resistant to growth in tissue culture compared, for example, to other epithelial cells from skin and breast. For that reason most studies on colonic epithelial cells have been performed using organ culture of tiny, millimeter sections of the epithelial layer (Autrup, H., et al. (1978) Gastroenterology 74:1248–1257; Browning, T. H., et al. (1969) J. Clin. Invest. 48:1423–1432; Deschner, E., et al (1963) J. Clin. Invest. 42:1922–1928; Deschner, E., et al. (1972) J. Natl. Cancer Inst. 48:1567–1574; Eastwood, G. L., et al. (1973) Gastroenterology 64:375–382; Usugane, M., et al. (1982) Digestion 24:225–234). Very recently a new method of culturing colonic crypts and crypt fragments in suspension culture has been described (Moyer, M. P., et al. (1983) Proc. of the Soc. for Exp. Bio. and Medicine 174,12–15). In both cases there is difficulty in visualizing single cells for analysis, as these methods maintain the three-dimensional crypt structure, a hollow cylinder of roughly 600 to 800 epithelial cells.

The organ culture biopsies are embedded and then sectioned from the base to the top of the crypt, a laborious procedure for processing numerous biopsies. However, such studies have shown that patients at very high risk for developing colon cancer because of inherited genes, and genetically low-risk individuals in cancer-free families, exhibit differences in the distribution within the colonic crypt of their DNA synthesizing cells. Differences in the location and the fraction of replicating cells have proven to be the earliest preneoplastic alterations seen during the evaluation of human colon cancer (Deschner, E., et al. (1975) Cancer 35:413–418; Lipkin, M., et al. (1974) Cancer 34:878–888; Lipkin, M., et al. (1983) Cancer Research, 43:1899–1904).

SUMMARY

The invention concerns a method for the routine primary culture of human colonic epithelial cells within a monolayer. 12-0-tetradecanoylphorbol-13-acetate (TPA) enhanced DNA synthesis an average of 8 fold when assayed by [$^3$H]dThd labeling indices (L.I.) in colonic epithelial cells from familial polyposis patients and in tubular adenomas. No such stimulation by TPA was seen in cells from high-risk patients without familial polyposis, or in cells from low-risk subjects.

DESCRIPTION OF DRAWING

FIG. 1 compares labeling indices of patients at varying risk to develop colon cancer.

DESCRIPTION

We have improved the prior method which has effected the growth of human colon tumor cells by the development of methods for the routine short-term tissue culture of normal colonic epithelial cells. Examples show culture of genetically distinct population groups at varying risks for developing colon cancer. Therefore, the culture of these normal colonic cells includes the culture of various preneoplastic cell populations as well. We then determine which agents, modulate DNA replication, antigen expression, and cytoskeletal organization in cells fro these patients. The material herein incorporates by reference the work in Cancer Research, September 1984 by Friedman, E. et al.

Tumor promoters exhibit diverse biological and biochemical properties in vivo and in vitro (Boutwell, R. I., (1974) CRC. Crit. Rev. Toxicol. 2:419–443; Weinstein, I. B., et al. (1979) in Carcinogens: Identification and mechanisms of Action p. 399 New York Raven, Press). They appear to effect these changes by binding to specific cell surface receptors (Blumberg, P. (1980) CRC. Crit. Rev. toxicol. 1:153–197), which also exhibit a calcium and phospholipid-dependent protein kinase activity (Niedel, J. E., (1983) Proc. Natl. Acad. Sci. USA 80:36–40; Takai, Y., et al. (1979) J. Biol. Chem. 254:3692–3695). Activation of this kinase is believed to start a cascade of intracellular changes leading to alterations in gene expression. In the vast majority, if not in all cases, colonic carcinomas in man arise within colonic adenomas or benign tumors (Muto, T., et al. (1975) Cancer (Phila.), 36:2251–2270). In carcinomas, and in the histological classes of adenoma believed to directly proceed carcinoma, TPA induces secretion of a plasminogen activator (Friedman, E., (1981) Cancer Research 41:4588–4599; Friedman, E., et al. (1984) Cancer Res. in press.). This protease causes alterations in cell morphology and concomitant destruction of the extensive cellular networks which characterize benign tumors. Cell to cell communication (Friedman, E., et al. (1982) Cancer Res. 42:5096–5105), and the actin networks connecting many adjacent cells are both disrupted (Friedman, E., et al. "Actin organization in Premalignant and Malignant Human Colonic cells" (submitted) and thus these TPA-treated adenoma cells resemble carcinoma cells.

Very benign tumors, in contrast, exhibited a mitogenic response to TPA (Friedman, E., (1981) Cancer Research 41:4588–4599). We study the response to TPA of normal colonic epithelial cells and various preneoplastic but nontumor colonic epithelial cell types. To perform this study we have first developed a method to reproducibly place into primary culture colonic epithelial cells from normal individuals and from patients with various genetic syndromes predisposing them to develop colon carcinoma.

One of the best studied of these inherited syndromes is familial polyposis (FP). Patients with familial polyposis almost invariably develop colon cancer. This rare disorder, affecting approximately one in 10,000 individuals, is nonetheless an important model for colon carcinoma development. This disorder manifests itself in the colon by a sequence of morphologically and functionally distinguishable normal cell preneoplastic stages (Bussey, H. J. R., et al. "Familial polyposis Coli in Gastrointestinal Tract Cancer" ed by M. Lipkin and R. A. Good, Plenum, New York City, pp. 279–294). The earliest change observed is a simple one. Normal cells in the normal colon cease cell division in concert with differentiation as they migrate up the crypt to become part of the gut wall. In FPs patients cell division continues as the cells migrate up the crypt onto the surface of the gut.

The term polyposis is used because the next distinguishable change is the appearance of hundreds to thousands of polyps in the affected colon. These polyps are benign tumors or adenomas. The earliest found, smallest and most abundant type of benign tumor is the tubular adenoma. These are first seen as tiny, millimeter-wide projections into the gut lumen. The high number of these benign tumors insures that one will progress through the later stages in carcinoma development during the lifetime of the patient.

Adenomas are found frequently in the general population, but all the changes which occur in the colonic epithelium preceeding adenoma formation are unknown. We have speculated that the proliferative disorders seen in the FPs crypt lead, possibly by additional genetic and promotional changes, directly to formation of the elongated crypts characteristic of the tubular adenoma even in individuals without familial polyposis. Thus we propose that the FPS preneoplastic stage(s) would occur in very localized areas of mucosa in non-polyposis patients, and at significantly lower frequency than in familial polyposis patients. This hypothesis was tested by asking whether the FPs colonic epithelium and tubular adenoma cells shared any common features. In an earlier study, each of four tubular adenomas were stimulated to divide by TPA (Friedman, E. (1981) Cancer Res. Supra). The following examples serve to illustrate the invention without limiting it to the specific examples shown.

Tissue culture procedures: Colonic mucosal biopsies were placed into cold 20 mM Hepes-buffered Dulbecco's modified Eagle's medium immediately upon removal from the patient for transport to the laboratory. The biopsies were washed three times with antibiotic-containing wash medium (Friedman, E., et al. (1981) In Vitro 17:632-644), then minced into tiny fragments about 0.5 mm in diameter with two scapels. The minced tissue was placed in a 15 ml sterile conical centrifuge tube containing 3 ml wash medium, 1 ml hyaluronidase (300 units, Type IV, Sigma), 1 ml collagenase (600 units, Type IV, Worthington), and 1 ml neuraminidase (4 units, Type V, Sigma). The enzymes are used at a lower concentration and for a shorter time for digesting flat mucosa from normal, high risk, and familial polyposis patients in contrast to that used previously for digestion of adenomas and carcinomas. The tissue can be digested in a mixture consisting of equal 1-, 2-, 3-, 4 or 5 ml and the like aliquots of each enzyme plus wash medium depending on the size of the packed volume of cells (1-5 ml). The tissue digest was warmed at an elevated temperature for a time, for example, at 37° for 10 minutes, then digested for between 30 to 60 minutes (with 1 hour being the preferred time) at a lower temperature such as room temperature while on a tube rotator at 24 rpm. The rotation helps to release lymphocytes from the intercryptal spaces during the digestion. Obviously, any gentle agitation will be an equivalent. After digestion the tissue was composed of small groups of adherent crypts and partial crypts.

The digest was washed by pelleting at 100x g for 2 minutes, then resuspended in 10 ml wash medium and repelleted. The wash medium was aspirated off and the digested crypts resuspended in enough warm 168 growth medium to allow 0.2 ml of digest to be plated in each petri dish. Depending on the number of biopsies, 6 to 12 petri dishes were seeded. The digest was mixed between each aliquot to insure equal amounts of tissue are plated in each dish. 35 mm Corning petri dishes coated with a thin layer of 0.1% gelatin can be used as an example of a growth-compatible surface coating of a cell growth container (such as a petri dish) to allow explant attachment.

The digested fragments in 0.2 ml of medium were allowed to sit undisturbed for 30-45 minutes in the incubator at 37° to allow attachment of the crypts onto the coated petri dishes. Then 1 ml of warm 168 growth medium was added to each plate plus any additives and the dishes were left undisturbed for between 24-30 hours to allow migration of the epithelial cells. The growth medium was NCTC 168 (K.C. Biologicals, Lenexa, Ka.) supplemented as described (Friedman, E., (1981) Cancer Res. 41:4588) with fetal calf serum, transferrin, insulin, hydrocortisone, epidermal growth factor, and selenous acid. Deoxycholic acid at $8 \times 10^{-9}$M and pentagastrin at 250 micrograms/ml were added. TPA, its analog 4alpha phorbal didecanoate (4alphaPDD), and [$^3$H]dThd were purchased, stored, and used as described (Friedman, E. (1981) Cancer Res. Supra). An average of 19.2 epithelial patches grew per biopsy. Biopsy specimens were removed from the rectosigmoid colon as described (Deschner, E., et al. (1963) J. Clin. Invest. 42:1922-1928). The population groups used in this study have also been described (Lipkin, M., (1974) Cancer 34:878-888; Lipkin, M., et al. (1983) Cancer Research 43:1899-1904).

Autoradiography: Cells were grown in the presence of 5 microCi/ml [$^3$H]dThd (20 Ci/mmole,NEN) for 30 hours, fixed by two exposures to methanol for 10 minutes, covered with undiluted NTB-2 nuclear track emulsion (Kodak), exposed for 10 days to 2 weeks, developed and stained with filtered hematoxylin. All of the experiments were number coded by one individual and scored by a second individual with no knowledge of the source of the biopsy or the experimental details. Data from two experiments scored by two different observers differed at most by 15%. The average number of cells scored after autoradiography per biopsy was 6174 which is roughly equivalent to 8 to 10 complete crypts.

EXAMPLE I

Reproducible Conditions for Primary Culture of Human Adult Colonic Epithelial Cells We have routinely obtained 6 to 10 parallel primary cultures from 91% (85 of 93) of colonic mucosal biopsy specimens removed from human adults. These biopsies were obtained by endoscopic biopsy from the rectosigmoid region of the colon. They typically were no more than 3 mm in diameter and included only the epithelial layer (mucosa) and not the underlying colonic muscle or submucosa. Biopsies were obtained from normal subjects, subjects at increased or decreased risk for colon cancer on the basis of familial association, and others symptomatic or at-risk for familial polyposis. No differences were noted among these groups with regard to the capacity of their colonic epithelium to be cultured.

The minced, digested tissue formed a monolayer around a small explant after overnight culture. Phase contrast micrography at ×320 magnification of a monolayer of living adult human colonic epithelial cells from a nonpolyposis patient shows that the cells have migrated onto the petri dish to form a monolayer from the explant during the 24 hours of culture. The explant is a group of colonic crypts which appear as adjacent cylinders slightly out of focus as the plane of focus is on the monolayer (×320 magnification). Occasionally a small patch of cells also adhered without an explant. The sizes of the monolayers varied considerably from about 200–4000 cells, with the median value of approximately 350 cells. The explant typically consisted of a group of several adjacent crypts. In marked contrast when colonic mucosal biopsies of familial polyposis symtomatic patients were subjected to the same digestion protocol, individual crypts and portions of crypts were obtained. Phase contrast micrography at ×314 magnification of a colonic crypt freed by digestion of a mucosal biopsy of a familial polyposis patient, uses digestion conditions above. The crypt was in culture 6 hours before photography so its shape is largely maintained although some cells can be observed to have begun migration onto the culture dish in another plane of focus (×314 magnification). The adhesiveness of crypts to one another therefore appears decreased in familial polyposis colonic epithelium.

The cells which migrated from the explants formed small monolayer patches contiguous with the explant. The cells were usually close-packed and polygonal within these patches, but the cells occasionally were not contiguous. Phase contrast micrography of a colonic epithelial cell monolayer extending from an explant reveals areas within the monolayer exhibiting gaps with noncontiguous cells (×640 magnification). This interrupted monolayer was clearly different from the continuous monolayer formed around explants of benign colonic tumors under similar culture conditions (Friedman, E., et al. (1981) In Vitro 17:632–644).

Monolayers from biopsies of a normal subject and a familial polyposis subject were analyzed by electron microscopy. Both contained typical epithelial structures. The normal colonic epithelial cells were connected at their lateral edges by a junctional complex:- tight junction, gap junction and desmosome in that order. Flask-like goblet cells full of mucus droplets at the apical region were observed. A brush border was elaborated at the apical end of the cell where mucus strands were also apparent. A basement membrane was also seen under the epithelial layer. These structures were also seen in the familial polyposis epithelium. The migrating cells slid from the explant like a stack of falling dominoes so that one cell often slightly overlapped the adjacent cell. Only at the edge of the monolayer were the flattened cells apparently not overlapping.

Cultured colonic epithelial cells were able to synthesize DNA. Epithelial cells remain capable of incorporating [$^3$H]dThd for at least seven hours after plating, or nine hours after removal from the patient. They have lost this capacity by 19 hours after removal from the patient. They have lost this capacity by 19 hours postplating. 3H-Thymidine labeling indices (L.I.) of colonic biopsies from three patients were 6.4%, 20.1%, and 12.3% when the label was added upon plating. In each case the L.I. was 0% when the label was added 19–26 hr postplating. In one case [$^3$h]dThd was added at plating, 3, 7 and 24 hours post-plating and labeling continued to 26 hours postplating. The L.I. (mean ± standard error) were respectively 12.3±5.5, 22.6±4.5, 23.7±6.2, and 0%. There was no difference between data obtained when the labeling was begun immediately post-plating or 7 hours later, indicating equal capacity to incorporate the label. Similar data were obtained from biopsies from two patients labeled from 0 hr and either 5 or 6 hours post-plating (not shown). These data imply that no cells enter S from $G_1$ under usual culture conditions so that only cells already in S phase were capable of DNA synthesis and incorporation of [$^3$H]dThd. If cells entered from $G_1$ under our culturing conditions the longer labeling times of 0–30 hours would have yielded higher L.I. than the 7–30 hours labeling period or the 5–30 or 6–30 hour labeling periods. This was not seen in any of the three experiments.

EXAMPLE II

Incorporation of [$^3$H]dThd into Nuclear DNA

The grains were always over the nuclei and not the cytoplasm suggesting the [$^3$H]dThd was incorporated into cellular DNA. To further demonstrate this point three parallel cultures from a biopsy were labeled, fixed as above, and then two were incubated with 240 units of RNAse-free DNAse I (Worthington) while the other was incubated in buffer alone (10 mM Tris-HCl at pH 7.2 with 10 mM MgCl$_2$) for 60 minutes at 37° C. After processing for autoradiography as above, the buffer treated control had a L.I. of 31.7% while the DNAase treated cultures contained no labeled cells in a total of eight colonies. In a second experiment parallel plates from a biopsy were labeled, methanol fixed, and one plate was extracted in 5 ml of 5% TCA for 10 minutes at 25° C. while the other control plate was left untreated. The L.I. for both plates were, respectively, 21.3% and 20.7%. These two experiments demonstrated that [$^3$H]dThd was incorporated into TCA insoluble, DNAase sensitive molecules concentrated in the nuclei. We conclude that the [$^3$H]dThd was incorporated into nuclear DNA. As an additional control the incorporation of [$^3$H]dThd into DNA was shown to be blocked by a prior addition of 100fold excess of unlabeled thymidine. Eight parallel plates were seeded from one biopsy. Unlabeled thymidine at $2.5 \times 10^{-7}$M was added to fourplates, followed by 5 microCi of [$^3$H]dThd at $2.5 \times 10^{-7}$M. The second set of four control plates was labeled at 0 hours with [$^3$H]dThd followed 2 hours later by the cold thymidine chase to control for the presence of the excess thymidine in the experimental plates. The mean L.I. of the cultures with excess unlabeled thymidine added before addition and 2 hours after addition of the label were respectively 0% and 17.2%. Therefore the 100fold excess of unlabeled thymidine prevented incorporation of the labeled base if added prior to the label. Two hours was arbitrarily chosen as a minimum time to get efficient labeling before addition of the cold thymidine. No deleterious effects of the cold thymidine on either DNA synthesis or migration were observed. The size of the epithelial patches grown in cold thymidine averaged 590 cells, which is within the normal range seen in this study and the L.I. of 17.2% was close to both the mean and median values of the HRa group in which the patient fell, 17.2% and 16.4% respectively (see following section).

EXAMPLE III

[$^3$H]dThd Labeling Indices of Colonic Biopsies in Monolayer Culture Distinguish Among Different Patient Groups L.I. were obtained from 43 patients. These include 8 patients with intestinal polyposis termed FPS (familial polyposis, Gardner's syndrome, and a single case of Peutz-Jeghers syndrome); 4 subjects in FP families free of disease but at risk becuase of familial association termed FPa; 11 patients symptomatic with either carcinoma or adenomas with or without a family history of colon carcinoma termed HRs (high risk symptomatic); 15 subjects asymptomatic for carcinoma or adenomas, but with a family history of colon or other cancers termed HRa (high risk asymptomatic); and 5 subjects from families colon cancer free for two or more generations considered at low risk for developing colon cancer termed LR. The mean L.I. for each patient and the mean value of each group are determined. FPs patients and LR subjects had mean L.I. of 5.2% and 5.7% respectively. These were much lower than the mean L.I. of the FPa subjects and both the HRa and HRs subjects. They were 14.4%, 17.2% and 12.2%, respectively. The Wilcoxon rank test was used to determine whether the groups were distinguishable by L.I. The FPs group was statistically different from the FPa, HRs, and HRa groups with p values less than 0.01, 0.005, and 0.001 respectively. HRa was distinguishable from HRs at the 0.05 level of discrimination, presumably because some symptomatic patients had low L.I. which overlapped with the LR subjects. In contrast FPs was indistinguishable from LR (p less than 0.1). The L.I. appeared to characterize an individual if the same area of the colon was biopsied again. One HRs patient was biopsied in the rectosigmoid colon twice, with a seven month interval. The L.I. (standard error) were respectively, 6.9 (2.6)% and 8.2 (0.4)%, identical within statistical variation.

EXAMPLE IV

TPA Enhanced DNA Synthesis in Familial Polyposis Epithelium but not in Normal Epithelium The tumor promoter TPA has been used to distinguish between preneoplatic cells at different stages of tumor development. In primary culture, carcinoma cells and premalignant dysplastic cells within benign tumors (adenomas) respond to TPA by secreting a plasminogen activator (PA). In contrast preneoplastic adenoma cells from benign tumors at an earlier stage in tumor evolution than premalignant dysplastic cells, responded to TPA by enhanced proliferation (Friedman E. (1981) Cancer Res. Supra; Friedman, E., et al. (1984) Cancer Res. Supra). We asked whether the proliferative response to TPA was seen first during tumor evolution in adenoma cells or whether it characterized an even earlier stage, such as FP epithelium. Therefore at the time of plating either TPA or its inactive analog 4alpha PDD was added to parallel cultures from 6 FPs patients, 6 HRs patients, 7 HRa subjects and 5 LR individuals and the L.I. determined (Table I). In an initial experiment 50 ng/ml TPA, an effective dosage for adenoma proliferation, was added to cultures from LR subject 719. The L.I. of the TPA treated cultures was lower than that of the analog treated cultures os the dosage of TPA was lowered to 10 ng/ml for all subsequent experiments to avoid any possible toxicity. TPA at 10 ng/ml induced PA secretion from adenomas in an earlier series of experiments (Friedman, E. (1981) Cance Research 41:4588-4599) demonstrating the effectiveness of this concentration of TPA on colonic epithelial cells.

Five of the six FPs patients exhibited L.I. which were enhanced an average of 8 fold by TPA treatment (Table IA). In the case of FPs patient 721, 1 ng/ml TPA also significantly (4-fold) stimulated DNA synthesis. This was less than the 7-fold stimulation seen when cells were grown in the presence of 10 ng/ml TPA. In a second FP case both the normal appearing epithelium and an adjacent tubular adenoma were tested with 10 ng/ml TPA. TPA enhanced the L.I. an almost equal degree with each tissue (5-7 fold). In contrast to these results the colonic epithelium of FPs patient 821 showed no enhanced proliferation by TPA addition. By the Wilcoxon signed rank t test for paired samples, the L.I. of the FPs patients including the nonresponsive 821 was significantly different when the culture was carried out in the presence of TPA (p less than 0.05). By this test there was no significant difference (p less than 0.05) between L.I. generated when either TPA or 4alpha PDD was present in the culture medium for the HRa, HRs or LR groups (Table IB-D). TPA was tested at 10, 1, and 0.1 ng/ml for HRa patient 773 with no significant effect. 10 and 1 ng/ml TPA also had no enhancing effect on DNA synthesis of HRs patient 720. A second tumor promoter which binds to the same receptors as TPA, teleocidin B (Umezawa, K., et al. (1981) Nature (London) 209:411-413), elicited no increase in L.I. when tested on epithelial cells from HRs patient 806 and LR patient 807 at 10 ng/ml.

TPA induced no morphological changes in either FPs or any other colonic epithelial cells tested in this study. In earlier work premalignant and malignant colonic epithelial cells in primary culture secreted a plasminogen activator in response to TPA. This secreted protease caused characteristic morphological changes including a rounding up of cells and detachment of some from the plate as cell clusters (Friedman, E., (1981) Cancer Res. Supra). No such changes were seen in the experiments described here so we hypothesize that no plasminogen activator was released from normal and FPs cells in response to TPA.

Colonic epithelium from five of six FPs patients were stimulated to undergo DNA synthesis by TPA. In one case the FPs normal length epithelium and an adjacent tubular adenoma were tested for response to TPA in parallel experiments. A similar enhancement of DNA synthesis was seen in both tissues, directly confirming a prediction of our model.

The one TPA-unresponsive FPs epithelial biopsy may indicate that there are two classes of FPs epithelial cells, one TPA-responsive, one not. A second possibility is that the biopsy was taken from an area of mucosa which does not express the polyposis mutation. Most FPs patients exhibit the syndrome in the vast majority of their crypts. A high degree of penetration of the mutation is expressed as a high proportion of altered colonic stem cells. However, in some patients the expression of the mutation is less general. This leads to patchy expression of the polyposis phenotype and uncertainty whether polyposis crypts or normal crypts are being biopsied.

Epithelial cells were not stimulated to divide by TPA from any of the five control grou patients at relatively low risk to develop colon cancer on the basis of a negative personal and family history of colon cancer. Both human (Mufson, R. A., et al. (1982) Cancer Research 42:4600-4605) and murine (Yuspa, H. S., et al. (1983) Cancer Research 43:5707-5712; Yuspa, H. S., (1982) Cancer Research 42:2344-2349) keratinocytes are stimulated to differentiate not proliferate by TPA so the lack of mitogenic response of normal colonic epithelial cells to TPA was not without precedent. We hypothesize that an endogeneous promoting agent which binds to the TPA receptor could increase the number of preneoplastic cells expressing the FPs mutation in vivo by selectively enhancing their replication. The surrounding normal cells would, in this model, be unresponsive to the mitogenic effects of the promoter. This model is consistent with clinical observations. Patients are not born expressing the FPs phenotype, but begin exhibiting colonic alterations in their teens and twenties.

In addition to the FPs patients at very high risk to develop colon cancer are other categories of patients judged to have a higher than average risk to develop cancer. This assessment is on the basis of high familial frequency of colon cancer. These we have grouped for simplicity into high risk groups either symptomatic with adenomas or carcinomas or asymptomatic. None of the 13 patients in these groups had colonic epithelial cells which responded by enhanced proliferation to TPA. Crypts from these patients more closely resemble those from control, low risk subjects than FPs patients in their susceptibility to enzymatic dissociation suggesting that FPs cells might be further advanced in preneoplastic development. To compare these groups further we have listed the general characteristics of each group—the labeling indices, DNA synthesis patterns, and response to TPA—of control epithelial cells and three classes of preneoplastic cells in Table III. These groups are placed into an order based on these characteristics although we have no direct evidence that any of the high risk symdromes predispose to FPs. However, we note that an early change predisposing to colon carcinoma is found in the high-risk nonpolyposis groups, and this change is less dramatic than that seen in the FPs colon. Proliferating cells are found all through the crypt length, not at the lower two-thirds as in normal crypts.

We postulate that some promoter-treated FPs cells eventually evolve into benign tumors and thus share some characteristics. Common features uniting FPs epithelium and tubular adenomas are (a) their proliferation is enhanced by TPA and (b) replicating cells in the crypts have reached the crypt surface and form part of the gut lumen. We assume that TPA stimulates cells to enter S phase from $G_1$ so they continue to cycle and ar inhibited from terminally differentiating. This is based on the observation that the L.I. of epithelial biopsies from FPs patients does not increase with continued time in the presence of the label in culture, suggesting thta only the cells in S phase continue to synthesize DNA unless TPA is present to stimulate their movement from $G_1$ into S phase.

The cells in the crypt are shed continually and only changes which affect the stem cells at the crypt base would cause permanent changes. We postulate that a feedback signal may occur from the TPA-stimulated cells at the gut lumen to the stem cells. Abrasion of the upper surface of the epidermis removes the terminally differentiated cells and leaves a layer of replication-competent cells. The keratinocyte stem cells at the bottom layer of the epidermis rapidly regenerate the upper, terminally differentiated layers (Argyris, T. S., (1981) CRC Crit. Rev. Toxicol., 9:151-200; Argyris, T. S., et al. (1981) Cancer Res. 41:5193-5195). These stem cells must be in functional contact with other cells in the layer to receive the signals initiating regeneration. The fact, epidermal cells in tissue culture are highly intercommunicating by gap junctions as shown by fluorescein dye injection into single cells in the monolayer (Steinberg, M. L., et al. (1981) J. Cell Physiol. 109:153-159). An analogous situation to epidermal abrasion may be initiated in FPs colonic cells by exposure to TPA. The cells in the uppermost region of the crypt have been made to replicate by TPA and the enhancement is considerable, averaging 8-fold in our studies. We assume that preneoplastic cells such as the FPs cells are highly intercommunicating in analogous fasion to preneoplastic adenoma cells (Friedman, E., et al. (1982) Cancer Res. 42:5096-5105). This intercellular communication would enable the colonic stem cells at the base of the crypt to be influenced by abnormal replication stimulated by tumor promoters at the top of the crypt. Thus, the replicating, non-terminally differentiated cells at the top of the crypt may affect the colonic stem cell just as the replicating cells at the upper layer of abraded epidermis affect the keratinocyte stem cells. The stem cells would receive signals to replicate and repopulate the terminally differentiated layer.

Stem cells in the colon have a good control of crypt length under normal circumstances. For example, in low-risk individuals rectal mucosal crypts are about 50 cells long. In FPs crypts stimulated with a tumor promoter the normal signals controling the crypt length might be lost, leading to overstimulation of the stem cell population, and to generation of elongated crypts. We know that the actin cytoskeletal organization patterns of FPs epithelium and adenomas of different histological classes are quite distinct. Therefore we hypothesize additional genetic or promotional changes are needed to progress from FPs to tubular adenoma. We have not directly tested the tumorigenicity of TPA-treated FPs epithelial cells because several benign tumor stages separate them from frank carcinoma.

Carcinomas are often seen to originate in situ within colonic adenomas. Villous adenoma cells are believed to have reached a more advanced preneoplastic stage than FPs epithelial cells because carcinomas are observed to arise within villous adenomas at a relatively high rate (e.g., 41%) (Muto, T., et al. (1975) Cancer (Phila.), 36:2251-2270). TPA-treatment of cultured villous adenoma cells was not sufficient to convert these cells to carcinomas capable of growth in a nude mouse. Several rounds of mutational changes followed by promotion in vivo may be necessary for normal colon cells to progress to carcinoma. Support for this hypothesis can be drawn from a well-controlled series of experiments which showed that mutatgenic treatment, but not promoter treatment, was necessary to convert benign mouse skin papillomas to carcinomas (Hennings et al (1983) Nature 304:67). Thus while we believe that promoter treatment of FPs cells may play some role in their evolution into benign tumors, it is unlikely to be sufficient to convert these cells to carcinoma cells.

EXAMPLE V

Comparison of [$^3$H]dThd Labeling Indices Derived from Organ Culture and from Tissue Culture The colonic biopsies taken from 12 patients were divided. Half of each biopsy was placed directly into organ culture while the remaining half was digested and then placed into tissue culture. For organ culture the colonic mucosa was carefully cut into 1 mm cubes, placed epithelial side up on a metricel membrane, and the placed on a rocking platform in 95% oxygen for 1.5 hr of [$^3$H]dThd labeling (Usugane, M., et al. (1982) Digestion 24:225-234). The tissue was then fixed, carefully sectioned lengthwise so the entire crypt was visible from the stem cells at the bottom to the lumenal surface, and then processed for autoradiography. Then the percentage of total labeled cells and their position within the crypt were tabulated (Usugane, M., et al.

(1982) Digestion 24:225-234). In contrast the remaining half of the tissue was minced, digested as described above for an hour, then allowed to attach and begin migration for 45 min in a thin layer of medium before the addition of growth medium and [$^3$H]dThd. After 30 hours of labeling some of the cells in the explant fragments had migrated onto the surface of the culture dish to form an epithelial monolayer. The cultures were then fixed in situ, coated with emulsion, and processed for autoradiography. The L.I. was determined solely on the cells in the epithelial monolayer patches. The labeling periods varied for both methods: 1.5 hr for organ culture and 30 hr for tissue culture. The long labeling period was necessary because the assay depends on formation of the monolayer by cells from the explant. We did not pulse-then-chase because removal of the label and washing led to detachment of the explants.

The values for L.I. by both methods clearly are not identical in the majority of cases (Table IIA). Although the labeling period was much longer in tissue culture the L.I. determined by this method were not uniformly higher. The data from two cases were identical while in 6 cases the tissue culture values were lower and in 4 higher. Although individual measurements were not identical, characteristic group differences in L.I. were still observed by both methods (Table IIB). The mean L.I. determined by organ culture for FPs (8.9) and LR (7.9) patients were lower then those for FPa subjects (13.9) and other patients at high risk (13.3). In analogous fashion the tissue culture derived L.I. data for these groups clearly differentiated the FPs (5.0) and L (4.5) patients from the FPa (14.7) and the nonpolyposis patients at high risk (22.8). The mean L.I. from the entire population studied by tissue culture methods is shown in the last column of Table IIB. See figure I for a comparison of labeling indices of patient categories.

EXAMPLE VI

DNA Synthesis is not a Necessary Precondition for Cell Migration

Occasionally epithelial patches would be seen which contained no labeled cells. In an extreme example of this observation, 9 of 13 4alphaPDD-treated colonies were unlabeled. In general all of the epithelial colonies contained labeled cells; in the case of HRs patient 826 this was 22 of 22. We wondered whether it would be possible to inhibit cell division in the explant by high concentrations of the mutagen mitomycin C and still get cell migration. Freshly prepared dilutions of $1.5 \times 10^{-4}$M, $1.5 \times 10^{-5}$M and $1.5 \times 10^{-6}$M mitomycin C were added to parallel cultures from two biopsies, A and B, which had been allowed to attach for 30 minutes. After 1 hour of exposure to the drug [$^3$H]dThd was added to all dishes plus control untreated plates. Labelling continued in the presence of the drug for 30 hours, and then the L.I. of all the cultures was determined. Both L.I. and colony size (mean ± standard error) for both specimens were decreased by $1.55 \times 10^{-5}$M mitomycin C with no decrease in the mean size of the epithelial patch. Neither parameter was affected by the lowest mitomycin C concentration. $1.5 \times 10^{-4}$M mitomycin C inhibited incorporation of the label 94% for biopsy A but did not decrease the average colony size. In contrast this concentration of the drug was cytotoxic for biopsy B as no outgrowth was observed and no labeled nuclei were observed within the explant. Heterogeneity in response to mutagens has been observed for colonic epithelial cells from different patients (Autrup, H., et al. (1978) Gastroenterology 74:1248) so this observation of differential sensitivity of patients A and B is not surprising. At the noncytotoxic concentrations of MMC for each biopsy, however, DNA synthesis was inhibited in the explant without subsequent inhibition of cell migration.

TABLE 1

EFFECT OF TPA ON [$^3$H]dThd LABELING INDEX IN POPULATION GROUPS

| PATIENT NUMBER | LABELING INDEX: MEAN (SE) | |
|---|---|---|
| | CONTROL | PLUS TPA |
| A. FAMILIAL POLYPOSIS SYMPTOMATIC | | |
| 752 | 10.9(2.7) | 68.8(11.6) |
| 724 | 0.2(0.2) | 3.4(2.0) |
| 766 | 9.0(2.3) | 25.3(10.6) |
| 746 | 4.1(1.9) | 27.7(6.9) |
| 746a | 4.0(0.6) | 21.4(4.9) |
| 721 | 2.5(1.1) | 16.3(4.8) |
| 721b | 2.5(1.1) | 9.6(1.9) |
| 821 | 3.7(0.8) | 1.8(1.2) |
| B. HIGH RISK SYMPTOMATIC PATIENTS | | |
| 826 | 9.9(1.7) | 11.1(1.9) |
| 720 | 16.4(3.2) | 25.6(5.8) |
| 720b | 16.4(3.2) | 13.7(5.4) |
| 754 | 12.2(1.3) | 2.0(1.4) |
| 805 | 7.0(1.5) | 4.3(1.1) |
| 748 | 29.2(2.8) | 30.4(5.4) |
| 806 | 13.1(3.9) | 6.4(1.5) |
| 806c | 13.1(3.9) | 0.7(0.6) |
| C. HIGH RISK ASYMPTOMATIC SUBJECTS | | |
| 761 | 28.8(6.1) | 18.4(3.3) |
| 762 | 13.0(5.8) | 9.4(3.3) |
| 760 | 17.7(10.7) | 29.3(3.7) |
| 814 | 6.8(0.9) | 12.2(0.5) |
| 773 | 18.5(3.0) | 25.7(3.2) |
| 773b | 18.5(3.0) | 16.3(5.7) |
| 773d | 18.5(3.0) | 19.7(3.1) |
| 774 | 14.5(4.2) | 23.5(3.1) |
| 774b | 14.5(4.2) | 28.4(6.6) |
| 815 | 18.1(4.1) | 20.1(4.4) |
| D. LOW RISK SUBJECTS | | |
| 722 | 1.5(0.6) | 0.0 |
| 722b | 1.5(0.6) | 0.2(0.2) |
| 719e | 8.8(1.7) | 5.0(3.6) |
| 758 | 3.1(1.5) | 8.3(3.6) |
| 807 | 10.1(1.7) | 9.8(1.2) |
| 807c | 10.1(1.7) | 6.6(1.7) |
| 819 | 5.2(1.6) | 3.0(1.2) |

The high-risk patients are symptomatic with adenomas or carcinomas or have a positive family history for colon cancer.
a, adjacent adenoma; b, 1 ng/ml TPA; c, 10 ng/ml teleocidin B; d, 0.1 ng/ml TPA; e, 50 ng/ml TPA
Unless otherwise indicated, all TPA additions were at 10 ng/ml and 4αPDD control analog added at 10 ng/ml.
SE = Standard error

TABLE IIA

COMPARISON OF [$^3$H]dThd LABELING INDICES DETERMINED BY ORGAN CULTURE AND BY TISSUE CULTURE

| PATIENT NUMBER | PATIENT CATEGORY | LABELING INDEX: MEAN (SE) | |
|---|---|---|---|
| | | ORGAN CULTURE | TISSUE CULTURE |
| 721 | FPs | 5.0(0.4) | 2.5(1.1) |
| 724 | FPs | 8.1(1.1) | 0.2(0.2) |
| 752 | PJs | 11.9(1.0) | 10.9(2.7) |
| 764 | FPs | 10.5(0.8) | 6.4(2.5) |
| 720 | HRa | 10.1(0.8) | 16.4(3.2) |
| 748 | HRs | 16.4(0.9) | 29.2(2.8) |
| 735 | FPa | 13.8(0.8) | 11.0(1.8) |
| 734 | FPa | 11.8(0.8) | 20.5(4.6) |
| 736 | FPa | 16.1(0.8) | 12.5(3.0) |
| 722 | LR | 6.9(0.5) | 1.5(0.6) |
| 719 | LR | 6.5(0.5) | 8.8(1.7) |
| 758 | LR | 10.3(1.2) | 3.1(1.5) |

TABLE IIB

SUMMARY OF DATA BY GROUPS
AVERAGE OF MEAN
LABELING INDICES

| PATIENT GROUP | NUMBER | ORGAN CULTURE | TISSUE CULTURE | MEAN TC |
|---|---|---|---|---|
| FPs | 4 | 8.9 | 5.0 | 5.2 |
| FPa | 2 | 13.9 | 14.7 | 14.1 |
| HRa + HRs | 3 | 13.3 | 22.8 | 15.1 |
| LR | 3 | 7.9 | 4.5 | 5.7 |

FPs, familial polyposis symptomatic; PJs, Peutz Jaegers syndrome which exhibits intestinal polyposis; HRa, asymptomatic patients with family history of colon cancer; HRs, patients symptomatic with either adenomas or carcinomas with or without a positive family history for colon cancer; FPa, asymptomatic at risk patient in familial polyposis family; LR, low risk for colon cancer. Number indicates the number of subjects compared from Table 11A.

The last column of the table under MEAN TC is a list of mean values for the labeling indices of all patients studied shown in FIG. 3A.

TABLE III

CHARACTERISTICS OF NORMAL AND PRENEOPLASTIC CELLS

| SYNDROME | TPA RESPONSE | MEAN L.I. | PROLIFERATION ZONE |
|---|---|---|---|
| Low Risk | None | 5.7% | Lower 2/3 crypt |
| High Risk | None | 15.1% | Throughout crypt, minor fraction at surface |
| Familial Polyposis | Growth | 5.2% | Throughout crypt and lumen surface |
| Tubular Adenoma | Growth | 4.0% | Throughout crypt and lumen surface |
| | | *23.4% | |

The data are taken from the tissue culture results of this study only, but are representative of earlier results (10, 13, 21). The data shown for the L.I. of tubular adenomas and indicated by * are the average of 6 values of cumulative L.I. from an earlier study (13) and fall within the range of values published by another group (4). The lower value found in this study was obtained by the same methods used for the biopsies of normal-appearing, so called "flat mucosa" detailed in Methods, and shown in Table 1A as 746a.

What is claimed:

1. Method for monolayer culture of normal human colonic epithelial crypt cells in tissue culture which comprises:
   (a) digesting said cells with a mixture of enzymes initially at an elevated temperature of about 37° C. for about 10 minutes and then at a lower temperature of about 25° C. for between about 30 minutes and about 60 minutes with an enzyme mixture no more than one-fifth the quantity used for colonic tumor cells comprising enzymes selected from the group consisting of hyaluronidase, collagenase and neuraminidase, wherein said enzyme mixture comprises an approximate ratio consisting of 300 units hyalurondase to 600 units collagenase to 4 units neuraminadase per 1–3 cubic millimeter biopsy;
   (b) mixing the digested cells with an amount of a growth medium sufficient to allow plating of the cell growth medium mixture; and
   (c) plating the cell growth medium mixture on an adhesive material, thereby creating a monolayer culture of normal human colonic epithelial cells.

2. Method of claim 1, wherein the growth medium is NCTC 168 which is supplemented with fetal calf serum, transferrin, insulin, hydrocortisone, epidermal growth factor, and selenous acid.